(12) United States Patent
Munir

(10) Patent No.: US 9,557,169 B2
(45) Date of Patent: Jan. 31, 2017

(54) METHOD FOR TRACKING DEFECTS ON A PHOTOMASK ACROSS REPEATED INSPECTIONS

(71) Applicant: Mohammad Saghir Munir, Union City, CA (US)

(72) Inventor: Mohammad Saghir Munir, Union City, CA (US)

(73) Assignee: RETICLE LABS LLC, Palo Alto, CA (US)

( * ) Notice: Subject to any disclaimer, the term of this patent is extended or adjusted under 35 U.S.C. 154(b) by 788 days.

(21) Appl. No.: 13/798,104

(22) Filed: Mar. 13, 2013

(65) Prior Publication Data
US 2014/0278209 A1    Sep. 18, 2014

(51) Int. Cl.
| | | |
|---|---|---|
| *G01C 9/00* | (2006.01) | |
| *G01B 21/20* | (2006.01) | |
| *G01B 11/24* | (2006.01) | |
| *G01N 21/95* | (2006.01) | |
| *G03F 1/84* | (2012.01) | |

(52) U.S. Cl.
CPC ............. *G01B 21/20* (2013.01); *G01B 11/24* (2013.01); *G01N 21/9501* (2013.01); *G03F 1/84* (2013.01)

(58) Field of Classification Search
CPC ................................ G01B 21/20; G01B 11/24
USPC ...... 702/150, 152, 94, 95, 159; 382/141, 149
See application file for complete search history.

(56) References Cited

U.S. PATENT DOCUMENTS

| | | | | |
|---|---|---|---|---|
| 5,966,677 | A * | 10/1999 | Fiekowsky | G01N 21/956 250/559.48 |
| 6,405,153 | B1 * | 6/2002 | Fiekowsky | G01N 21/956 702/159 |
| 2008/0125993 | A1 * | 5/2008 | Namioka | G01N 21/95 702/81 |
| 2010/0282956 | A1 * | 11/2010 | Kimba | H01J 37/28 250/252.1 |
| 2011/0264404 | A1 * | 10/2011 | Yanai | G03F 7/7065 702/150 |
| 2013/0054186 | A1 * | 2/2013 | Den Boef | H01L 23/544 702/150 |
| 2013/0294677 | A1 * | 11/2013 | Urano | G01N 21/956 382/141 |

* cited by examiner

*Primary Examiner* — Gregory J Toatley
*Assistant Examiner* — Eman Alkafawi
(74) *Attorney, Agent, or Firm* — Firasat Ali; Creso Legal LLC

(57) ABSTRACT

This invention allows tracking of a defect across multiple inspections. The inventive solution translates every inspection record into a common set of fields that are first archived into a relational database. Then the defect coordinates from the inspection records of the same mask are all transformed into a common reference frame having the same origin and orientation with respect to the mask coordinate system. Following this, the defect having coordinates within a given tolerance distance are paired up and reported to the user.

9 Claims, 12 Drawing Sheets

Fig. 12

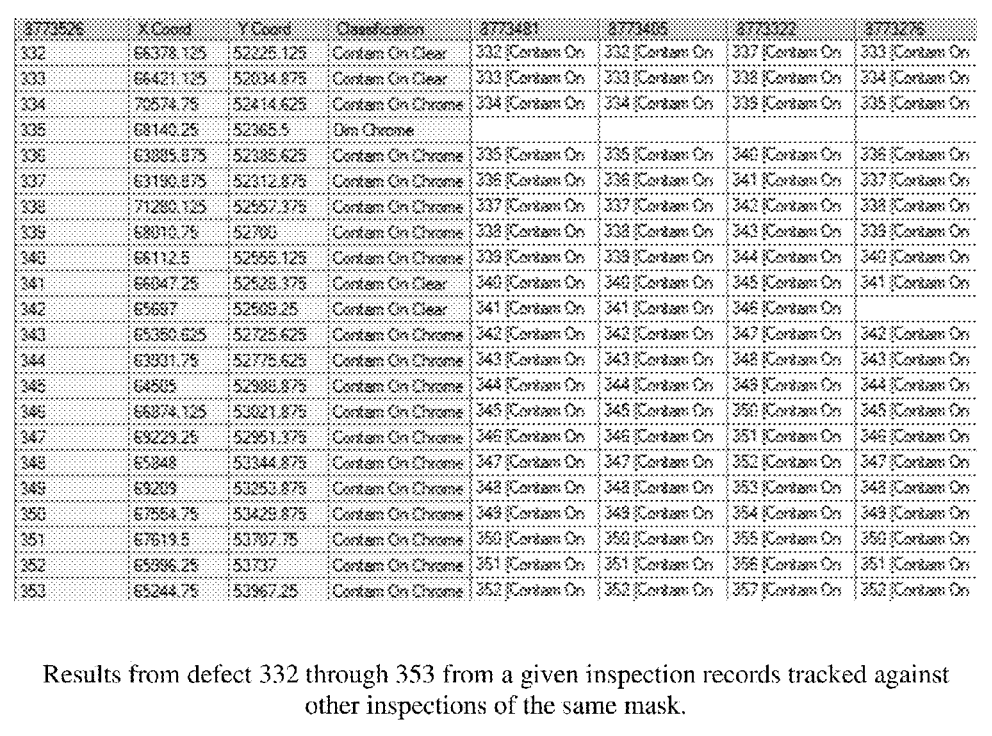

Results from defect 332 through 353 from a given inspection records tracked against other inspections of the same mask.

METHOD FOR TRACKING DEFECTS ON A PHOTOMASK ACROSS REPEATED INSPECTIONS

TECHNICAL FIELD

This invention relates generally to photo masks also known as reticles, commonly used in photolithography.

BACKGROUND OF THE INVENTION

Photolithography is a process by which integrated circuits are manufactured in the semiconductor industry. A photomask is an opaque plate with holes or transparencies that allow light to shine through in a defined pattern.

Lithographic photomasks are typically transparent fused silica blanks covered with a pattern defined with a chrome metal absorbing film. Photomasks are used at wavelengths of 365 nm, 248 nm, and 193 nm. This is shown as the light source 101 in FIG. 1, which then propagates through the exposure slit 102. Photomasks have also been developed for other forms of radiation such as 157 nm, 13.5 nm (EUV), X-ray and electrons and ions. As shown in FIG. 1, a set of photomasks 103, each defining a pattern layer in integrated circuit fabrication, is fed into a photolithography stepper or scanner and individually selected for exposure. Light passing through the photomask goes through the reduction optics 104. The outcome is a reduced pattern on the silicon wafer 105. Thus a photomask for an integrated circuit is like a negative for a photograph, which must be perfect.

Typically a high end photomask contains several defects. These defects may occur due to problems with the Mask writers or the photo chemistry used to etch the pattern. A photomask is typically written using an electron beam writer or a laser writer. Fluctuations in the beam current or laser voltage may induce non-uniform exposure in the photo resist. This may lead to unwanted discrepancies in the pattern. Alternatively, defects may be induced by the photo resist itself or even imperfection in the blank mask substrate. For EUV masks, defects in the blank substrate are very common, thus any pattern written on it will also be defective. A defect or unintended pattern on the photomask will propagate to all wafers exposed using it.

Photomask inspection or reticle inspection is an operation of checking the correctness of the fabricated photomasks to ensure that there are no defects in the pattern. This process is typically performed using a mask inspection system. Upon completion, the inspection system generates an inspection report (IR). As shown in FIG. 2, this IR report contains the sequential defect number, the X and Y coordinates of the defect with respect to known frame of reference 201, and sometimes an image of the defect and reference patterns. Typically the operator visually looks at every defect and assigns it a defect classification code that later aids in the mask making process. Since the wafer pattern is a replica of the photomask printed at a fixed reduction level, the wafer may also be used to check for defects found on the reticle. The bottom left corner of the mask is identified by 202. The inspection report may also contain coordinates of the alignment points 203 and 204 used to align the physical mask with the database reference pattern.

There are generally two modes in which the inspection systems operates. In the first mode, as shown in FIG. 3, the pattern on the mask, sometimes called a die, is compared against an ideal database reference pattern. This is generally referred to as a die-to-database inspection. In the die-to-database inspection the location of the defect 301 is precisely known.

In the second mode, a photomask having multiple repeated dies that can be compared to each other to look for defects. This mode of operation is called a die-to-die inspection, for which a database reference pattern is not required. If the dies are only repeated once, then comparing the left die with the right die, only concludes that there is a discrepancy between the two dies. This does nothing to indicate which of the two dies is indeed defective. As shown in FIG. 4, defect 401 in the left die and defect 402 in the right die are the same X and Y coordinate in each of the two identical dies. Using this method of error detection, the inspection tool will assume the left die is accurate and to be used as a reference and as such report the defect coordinate in the right die. This method has the limitation that the coordinate reported may be of the reference die. Therefore, the defect coordinate 402 must be translated by the die pitch distance 403 to accurately result in the defect location as represented by 401.

This problem however does not exist when the same die is repeated two or more times in the scanning direction, whereby through a process of elimination the exact die that contains the defect is automatically reported by the inspection tool.

A defect location is always reported, by its X & Y coordinate, with respect to a fixed reference point on the mask. This reference point may not be the same physical location and varies based on the type of inspection, the brand of the inspection tool, or even the choice of the operator. For patterned mask inspection the defect origin is generally defined by a special reference point feature 201 on the mask. When the inspection is started the stage of the inspection system is aligned to this reference point. For this reason the location of the defect is very precisely known with respect to the reference point.

Not all inspection systems use the same reference point as the origin. FIG. 5 shows a defect map where the reference point used is on the top left corner of the mask 501. Even though the defect map in FIG. 5 is identical to that shown in FIG. 3, the coordinates of each defect are much different because they have different origins (reference points).

Masks may be loaded into the inspection tool in various orientations. For example it may be that when the mask is covered with a pellicle, a transparent framed film to prevent micro contaminations from falling on the mask pattern, it may not be possible to load the mask in the standard orientation into the inspection system's stage. Other times, a given model of the inspection system may expect the mask to be loaded in a rotated orientation onto the stage. Regardless of the reason for the orientation change, the defect map looks rotated as shown by 601 in FIG. 6, when compared to FIG. 3 or FIG. 5. The orientation change induces a further level of complexity when matching defect locations across multiple inspections of the same mask. Not all mask inspections are done for the patterned masks. For advanced masks, it is important that the blank mask be inspected for defects before the pattern is etched on it. This is necessary to ensure that the blank mask does not have large defects on which it may not be possible to write a feature of the pattern. Since a blank mask does not have a reference point, the defect coordinates are given with respect to the bottom left corner of the inspection tool or some other coordinate frame origin such as the mask center. Since the bottom corner of the mask is not very well defined, or even its center, the location of the defect is not very precisely known. This is because there is no reference mark on the mask yet, to which the stage can be aligned (FIG. 7). To align the mask, an operator simply places the bottom corner 701 of the mask against the bottom corner of the stage of the inspection tool. This is an imprecise method of alignment since the mask can be offset either by particles trapped in-between the stage and the mask or due to other imperfections such as a physical gap. Thus finding a defect that is only a few tens of nanometers on a 154 mm by 154 mm mask, given its X & Y coordinates with respect to a poorly defined origin maybe difficult.

Multiple inspections of the same mask may be needed in the mask making process. For example, the mask may be inspected after the pattern is etched on it, and then any defects needing repair may be repaired, while others may be ignored due to being sub spec. After repair, and prior to shipping the mask, the mask undergoes a final inspection. During this time a repair site may be reflagged by the inspection system, even though upon manual measurement of the defect it may be sub spec. Thus it becomes necessary to track all repeated defects with the ability to match defects in one inspection against all prior inspections using the coordinates of the defects.

These repeated inspections ensure that a prior defect is properly dispositioned. Since there are multiple modes and tools used in inspecting a mask, the process of comparing defect locations becomes increasingly complex. For example, a mask loaded in one orientation during its first inspection may have been loaded in a different orientation in a subsequent inspection. Alternatively, a mask having a reference point near the bottom left corner during its first inspection may have a reference point near the top left corner in a subsequent inspection. Other times it may be necessary to compare defect coordinates on the blank mask against those detected after the pattern is written on the mask. If the defect locations match, than one can attribute the defects on the pattern mask to be due to a defect on the underlying mask blank substrate.

When the mask is shipped to the wafer fab, it too needs to be inspected on a routine basis. This is because one needs to know if new defects are appearing on the mask, that were not there before. Note that inspection systems generally detect many sub spec defects, which the operator manually classifies as being false. Thus, nearly all inspection reports contain defects, some of which are then classified as being false or sub specification. If a defect falls outside the specification, than the mask is sent back to the mask fab for repair.

It is to be noted that the various brands of inspection systems do not all generate an inspection report in a common output file format. For example, some tools write the inspection report as a plane ASCII text file, others may write a XML file, yet others may generate binary output files. Given that a semiconductor fabrication facility may inspect hundreds of photomasks in a given day, this alone presents a huge data management problem.

In order to perform the defect overlay analysis, a user would be required to individually load all inspection reports belonging to a given photomask manually. This alone would prove to be extremely cumbersome as a prerequisite to this exercise would involve saving inspection reports belong to the same mask either in the same file directory or naming all related inspections with a unique identifier as part of the file name, so that they can be found.

Furthermore, every time a new brand of inspection tool is introduced into the process, the defect overlay analysis software will need to be upgraded to be able to understand inspection reports from the new tool.

The alternative would have required multiple individual databases for each distinct inspection tool output format, which would then need to be individually queried to establish a relation between the various inspections of the same mask.

A method is needed that can relate all inspection reports from the various inspection system belonging to the same photomask efficiently.

For such repeated inspections it is highly desirable to compare and track defects across all prior inspection reports. However no current or prior art solution exists that can overlay defects across multiple inspections from various makes and models of inspection systems, having different reference points and orientation. Due to a lack of a viable solution, the knowledge gained by classifying defects in a prior inspection cannot be reused in a subsequent inspection, thereby creating an inefficient process requiring the operator to start from the beginning each time. Sometimes it may not be the mask that is inspected to look for repeated defects. Since the wafer pattern is an exact replica of the pattern on the mask, with a fixed optical reduction factor, inspection reports from the wafer inspection tool may also be used.

The engineers and technicians at a wafer fab generally like to match repeated defects against all previous inspections that were performed on a given mask or wafer, including those that were performed when the mask was being fabricated in the mask making facility. Thus there needs to be a way that makes accessible the multiple inspection performed at the mask fab to the operators at the wafer fabs.

Given that a mask can be inspected in the upright, rotated or inverted orientations, coupled with the problem of inspection systems reporting defects coordinates with respect to different reference points (i.e. origin of the reference frame), presents a huge challenge to the operator. Furthermore an advanced mask fab or a wafer fab can inspect hundreds of mask every day with each inspection containing up to tens of thousands of defects, presents a huge data management challenge on its own. Sifting through the various inspection reports to find the correct ones to compare, alone can take hours of the operators time. Dealing with the various reference frames and inspected orientations, and the intricacies of the various inspection system's output file format further makes this problem extremely difficult to deal with, for which no robust solution exists to date. Therefore, there is a need for a comprehensive solution that addresses the multitude of problems and inefficiencies described above in order to track defects across multiple inspections of the same mask.

SUMMARY OF THE INVENTION

A method for tracking a defect on a photomask or a wafer across a plurality of inspections is disclosed. The method involves receiving a plurality of inspection reports performed for the photomask. Each of the inspection report contains information relating to a defect on the photomask. If not tagged already, the inspection report is tagged with a unique identifier. Each inspection report may utilize a different defect reporting strategy. Alternatively, in one embodiment, more than two inspection reports containing the same defect reporting strategy may be produced.

The method further involves translating the received inspection report into a common set of fields. A relational database is populated with these common set of fields. Such translating and populating provides the user the ability retrieve the plurality of tagged inspection reports of the same photomask from the relational database by its unique identifier.

As a result, a single relational database that is capable of relating inspection reports from a variety of inspection tool brands can be created. This results in a more efficient database system, that can handle various output file formats, which can be easily queried. The alternative would have required multiple individual databases for each distinct inspection tool output format, which would then need to be individually queried to establish a relation between the various inspections of the same mask.

To match defects in repeated inspections of the same photomask, the present invention expresses all defects in the same base coordinate system. As a result, the system can handle inspection reports with the defects reported with respect to any origin, rotation, magnification or reference frame.

In one embodiment the present invention enables the user to overlay defects in repeated inspections, stored in the relational database, when defects in one inspection report has a frame of reference that is different from the defects in the other inspection reports.

As a result the system is independent of the coordinate system origin, rotation, magnification, or mirroring transformation used when reporting the defect coordinates.

In another embodiment the present invention allows the overlaying of defects between a die-to-die and a die-to-database inspections. If a match is not made in the first attempt, then the defects in the die-to-die inspection are moved to the alternate die and a second attempt to match the remaining defects is made.

BRIEF DESCRIPTION OF THE DRAWINGS

Features of the invention are more fully disclosed in the following detailed description of the preferred embodiments, reference being had to the accompanying drawings, in which like reference numerals designate like structural element, and in which:

FIG. 12. shows results from defect 332 through 353 from a given inspection report tracked against other inspections of the same mask;

Figure 1:
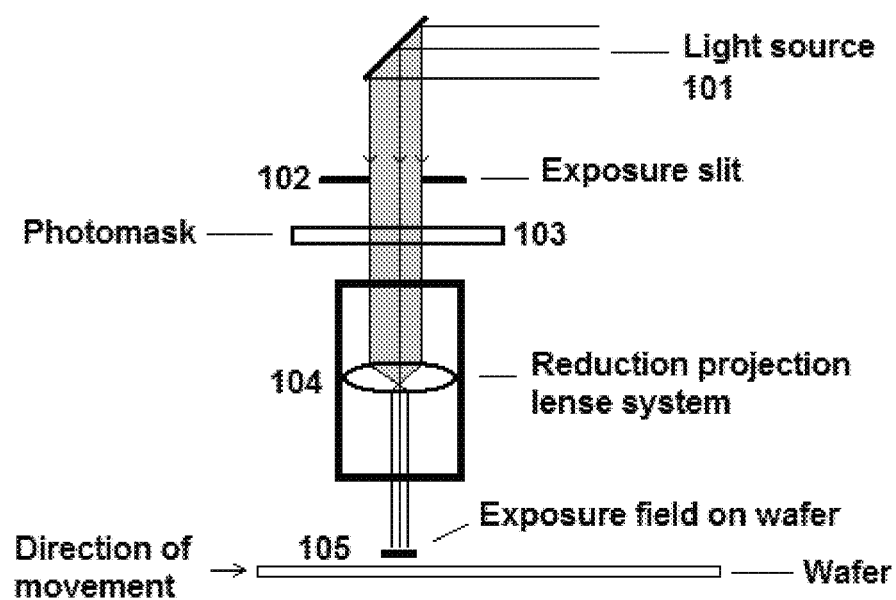
FIG. 1. is a schematic of a generic stepper-scanner used to imprint patterns onto a wafer using a photomask.
Figure 2:
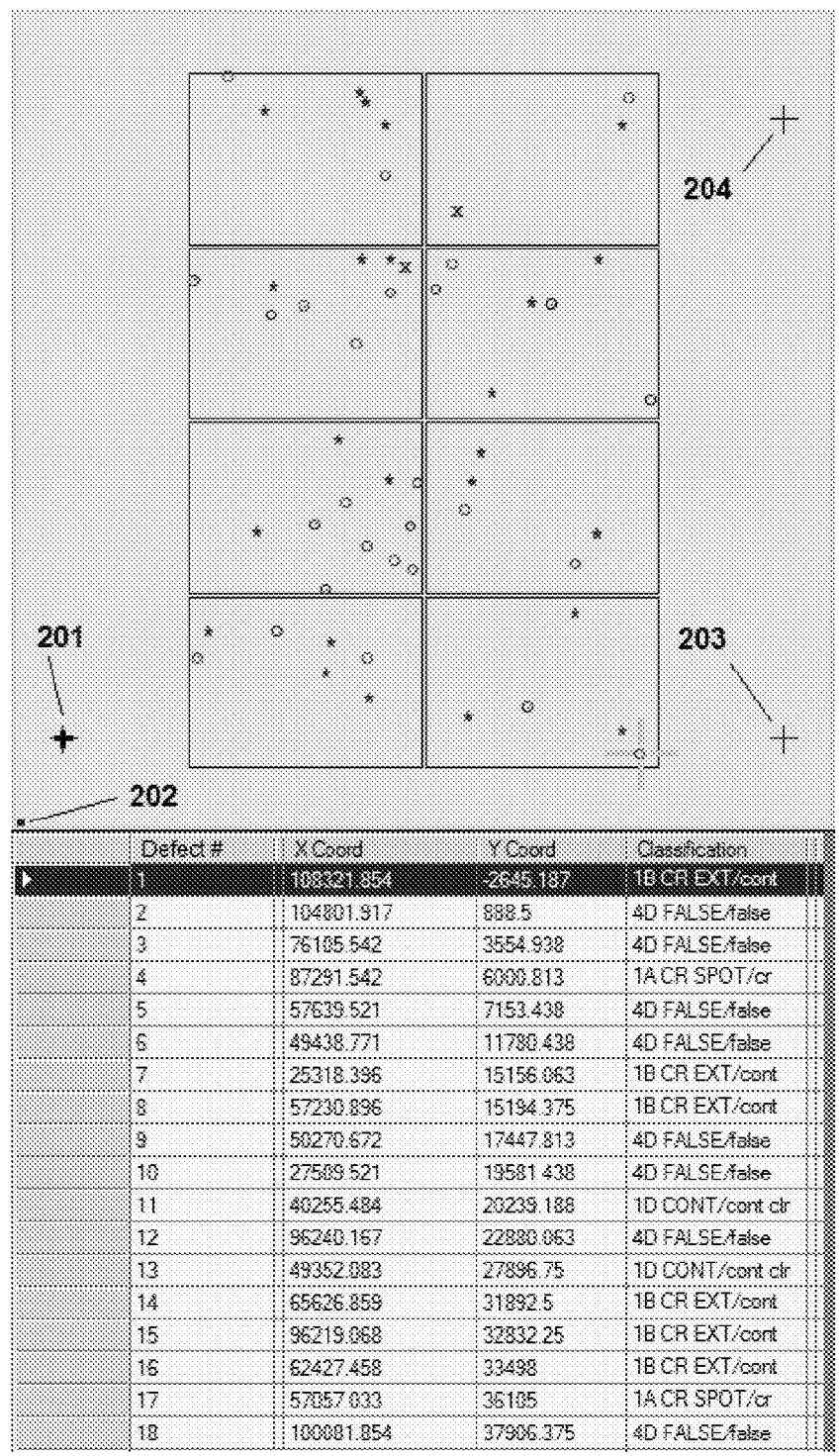
FIG. 2. is a sample mask inspection report generated from a mask inspection system rendered inside the client software showing the various points of reference and alignment.
Figure 3:
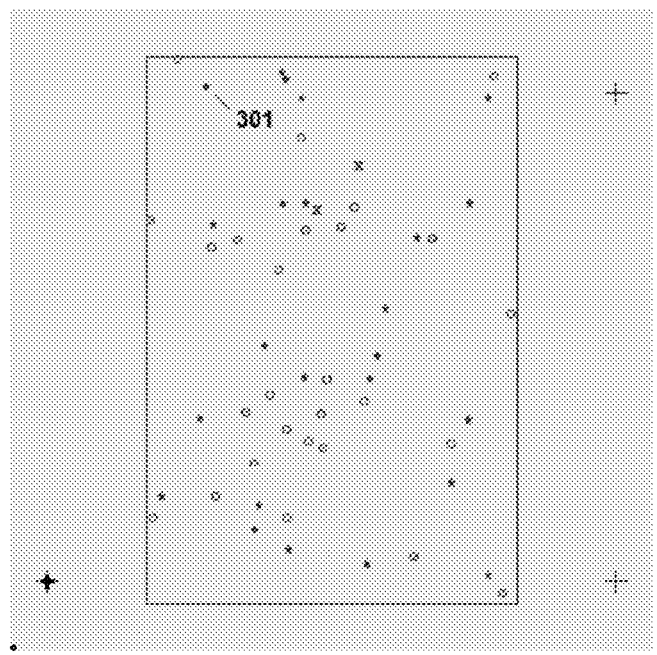
FIG. 3. is mask defect map from a die-to-database inspection mode.
Figure 4:
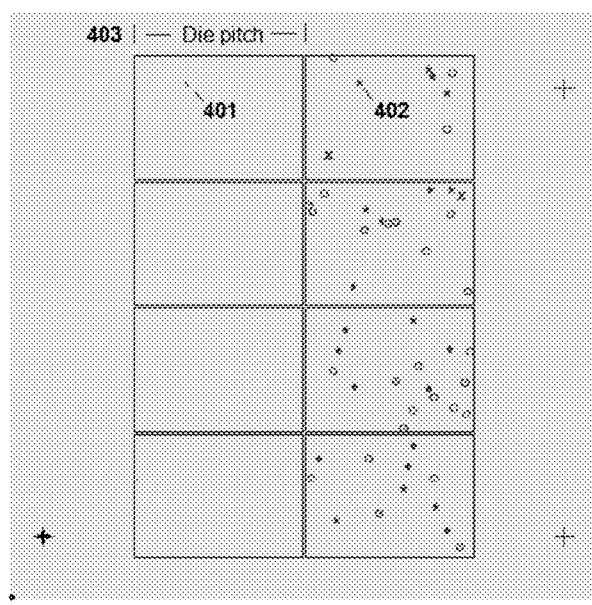
FIG. 4. is mask defect map from a die-to-die inspection mode.
Figure 5:
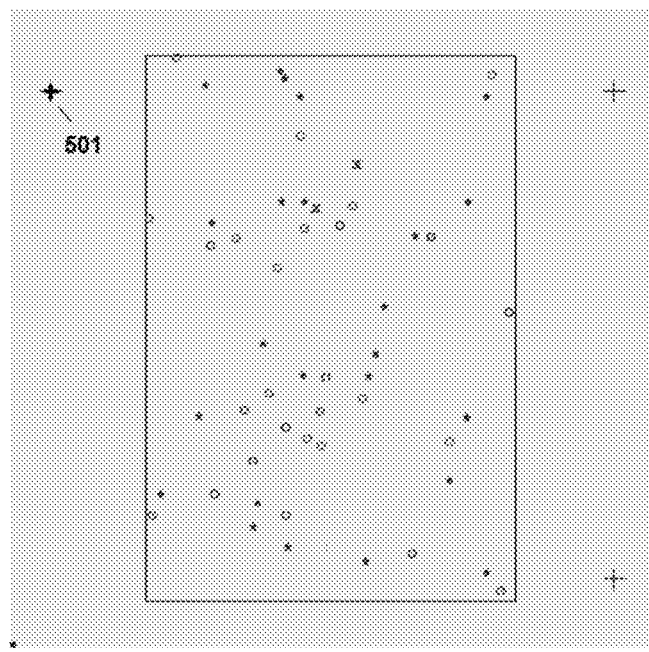
FIG. 5. is mask defect map with respect to an alternate reference point.
Figure 6:
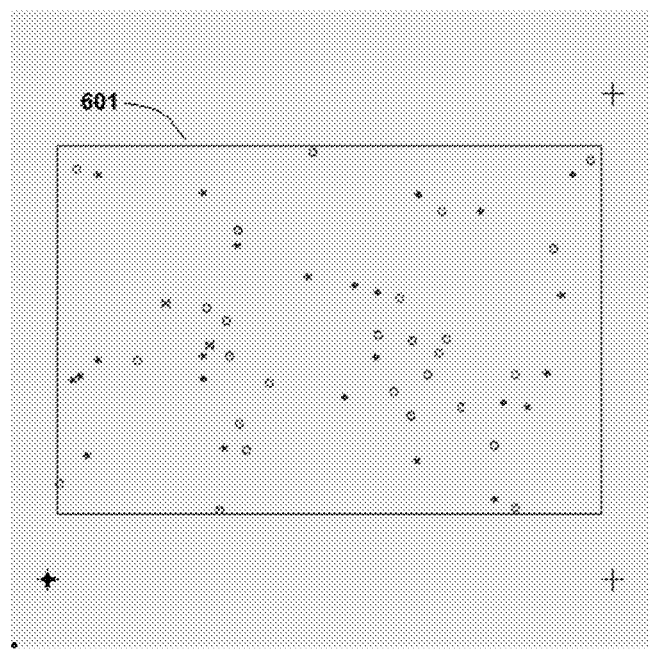
FIG. 6. is a mask defect map for an inspection performed with the mask either loaded 90 degrees counterclockwise or loaded on a different inspection system as shown in FIG. 3.
Figure 7:
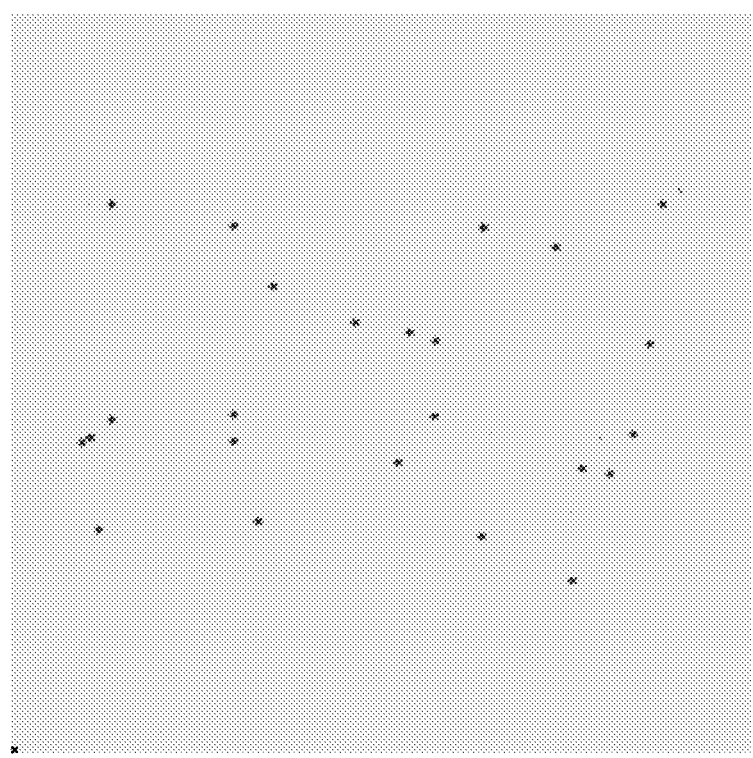
FIG. 7. is blank-mask inspection map for which there is no reference point and the defect coordinates are reported with respect to the approximate bottom left corner position or the approximate mask center position.

While the embodiments of the application are susceptible to various modifications and alternative forms, specific embodiments are provided as examples in the drawings and detailed description. It should be understood that the drawings and detailed description are not intended to limit the embodiments to the particular form disclosed. Instead, the intention is to cover all modifications, equivalents and alternatives falling within the spirit and scope of the invention as defined by the appended claims.

DETAILED DESCRIPTION

Specific exemplary embodiments of the invention will now be described with reference to the accompanying drawings. This invention may, however, be embodied in many different forms, and should not be construed as limited to the embodiments set forth herein. Rather, these embodiments are provided so that this disclosure will be thorough and complete, and will fully convey the scope of the invention to those skilled in the art.

The terms "mask" and "reticle" may be used interchangeably herein, and generally refer to a photomask used in microlithography.

Referring to the drawing figures, disclosed are apparatus 800 (FIG. 8.) and 900 (FIG. 9.), and methods 1000 (FIG. 10.) and 1100 (FIG. 11.) for tracking repeated defects across multiple inspection records from a variety of mask and wafer inspection systems.

Figure 8:
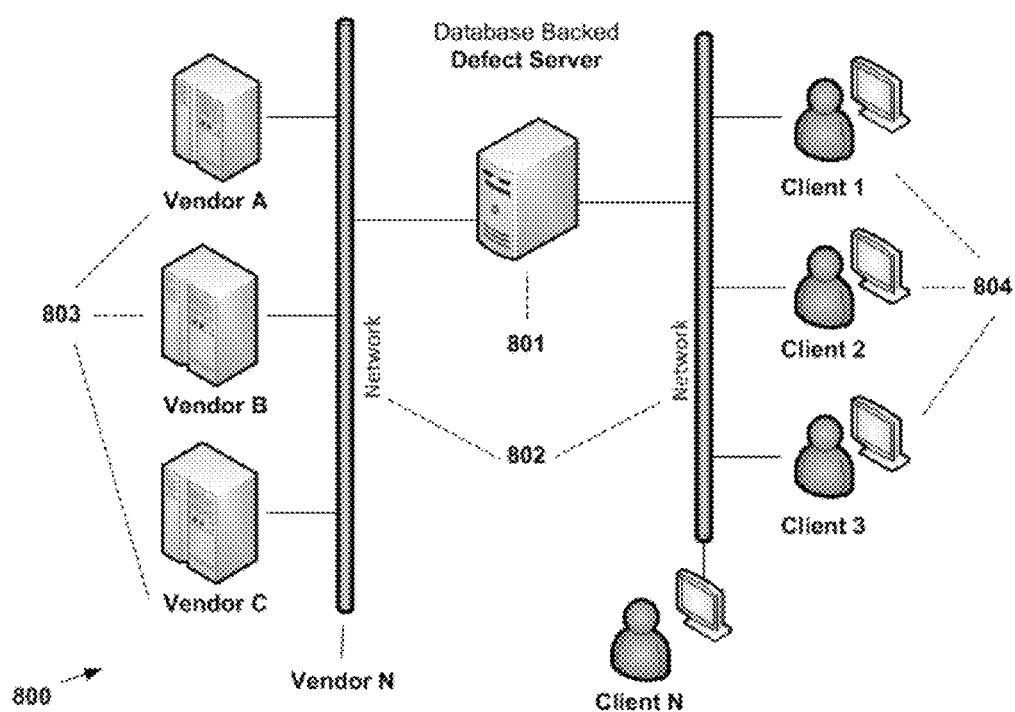
FIG. 8. shows inspection systems from various vendors connected to a defect server.

Referring to the apparatus in FIG. 8., various makes and models of the inspection systems 803 with a variety of configurations may be configured to write the inspection reports directly to a folder on the defect server 801 via the network 802. Alternatively the defect server may copy the latest inspection reports from the various inspection systems to a local folder. The users access the defect server via the client 804 software installed on their local personal computers, tablets computers or mobile devices. Alternatively the client software may be run via a remote desktop connection, a web browser or a hyper-terminal server.

Figure 9:
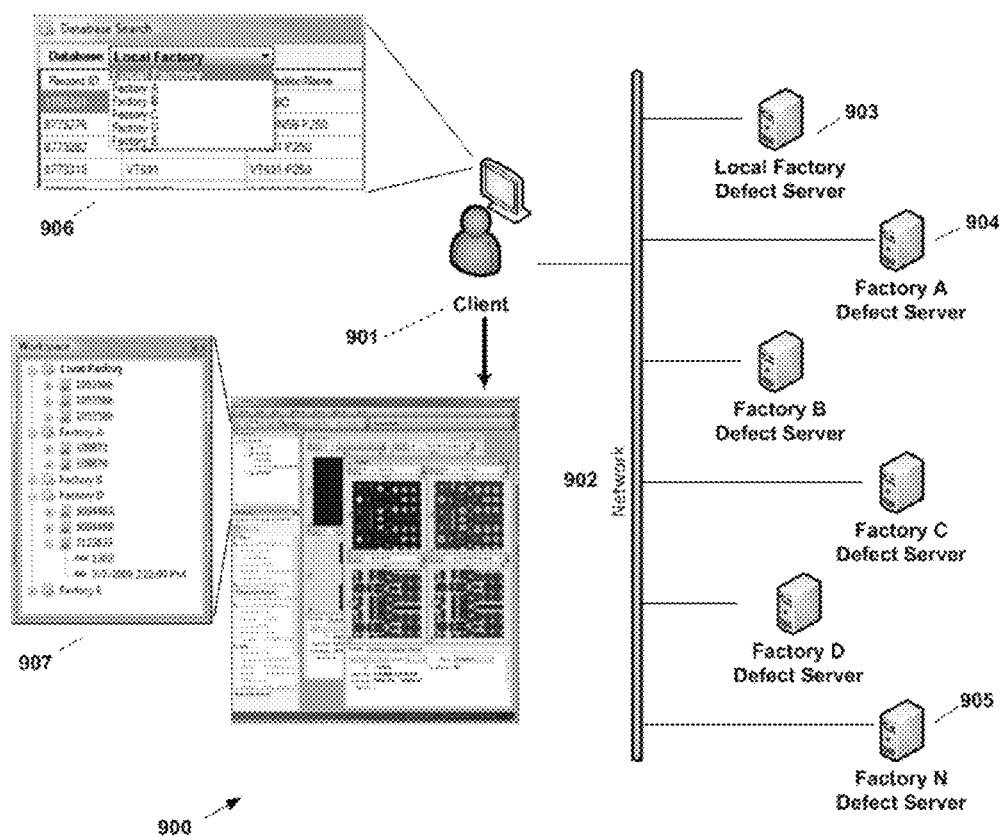
FIG. 9. shows the client software accessing data from an arbitrary number of defect servers.

FIG. 9 shows one embodiment of the architecture of how various defect servers within a large enterprise may be configured to share information is depicted. This feature allows operators at the wafer fabs to track repeated defects against all inspections starting with the blank mask substrate on which the mask pattern was written. Likewise engineers at the mask fabs can track defects on a given mask, even after the mask leaves the mask fabs, for future enhancements to the process. The client software 901 may access local defect servers 903 located within the factory, as well as other defect server at remote sites 904, over the network 902. The selection of which server to access may be made via the GUI interface 906 built into the client. For inspection systems that also capture defects of every image, the client is able to access these from the defect server and display them for the user. Within the client there exists a data tree 907 that outlines which inspection records have been loaded from the respective defect servers. The inspection records from each of the defect servers are listed under separate nodes within the workspace, with each node named after the respective defect server.

Figure 10:
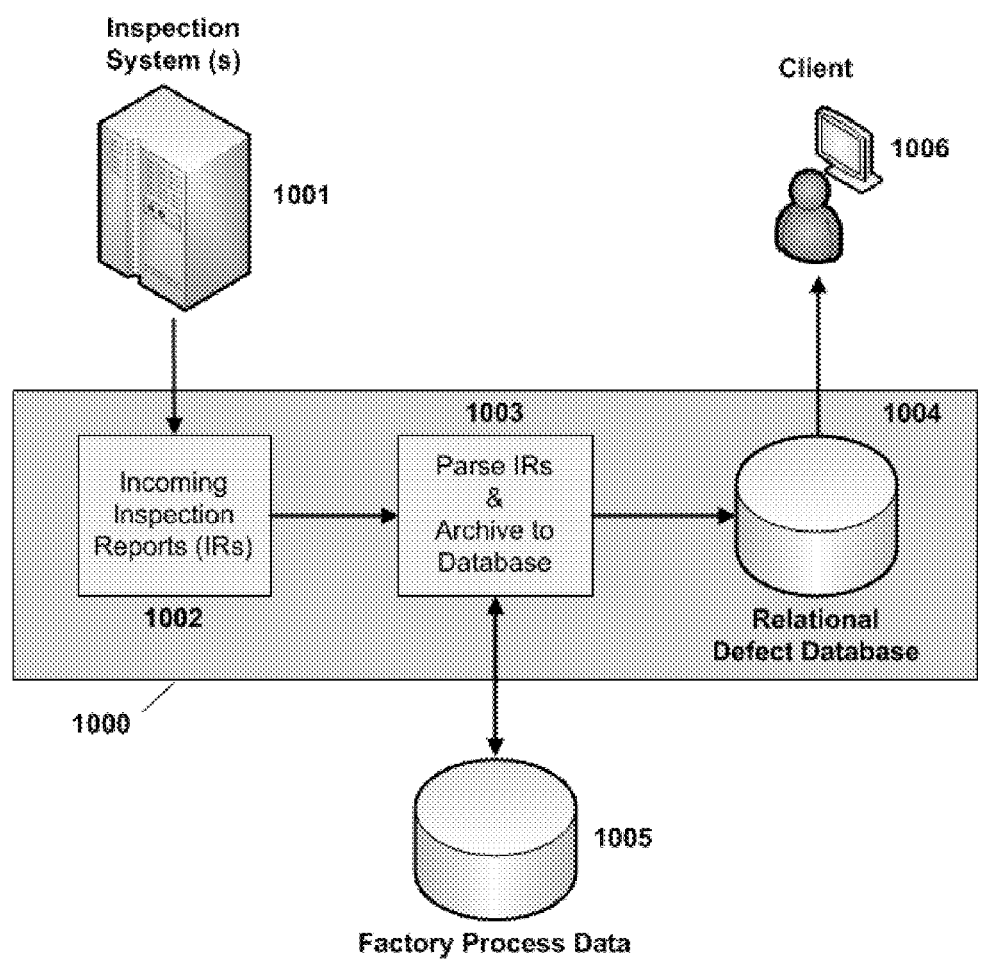
FIG. 10. shows the basic architecture of the server software.

In an embodiment a method by which data is populated into the defect server is outlined in FIG. 10. Inspection systems 1001 from various vendors write inspection reports 1002 to a folder on the defect server 1000. These inspection reports may not be in the same file format, as that depends on the make and model of the inspection system. Some inspection systems write plane text files, others follow a rigid file format, yet others write data in XML format and some even use binary files.

The job of the parser 1003 is to read the various inspection report file formats and distil every inspection report into a common set of fields, which are then archived into the relational database 1004. It is the contents of this relation database that are then accessed by the client software 1006.

Since a client needs to be able to retrieve all inspection records that belong to a given mask, there needs to be a unique field that identifies a given mask in every inspection record. Depending on the inspection tool used, an inspection report may or may not contain the unique identifier. In situations when the unique identifier is not present, the parsing software 1003 can query the Factory Process database 1005, using the inspection record's ID or other relevant fields, and retrieve the unique mask identifier, sometimes known as the product code or the mask barcode. Since all inspection records from the same physical mask contain the same unique identifier, all related inspections can be retrieved instantly from the relational database 1004. This makes it very easy for the operator to retrieve all previous inspections of the same mask for tracking repeated defects across multiple inspections.

A major task of the parser is to ensure that all inspection records in the database contain information about the frame such as, offset, rotation, magnification and mirroring information so that the defect coordinates can be translated to a common 'base' reference frame.

Figure 11:
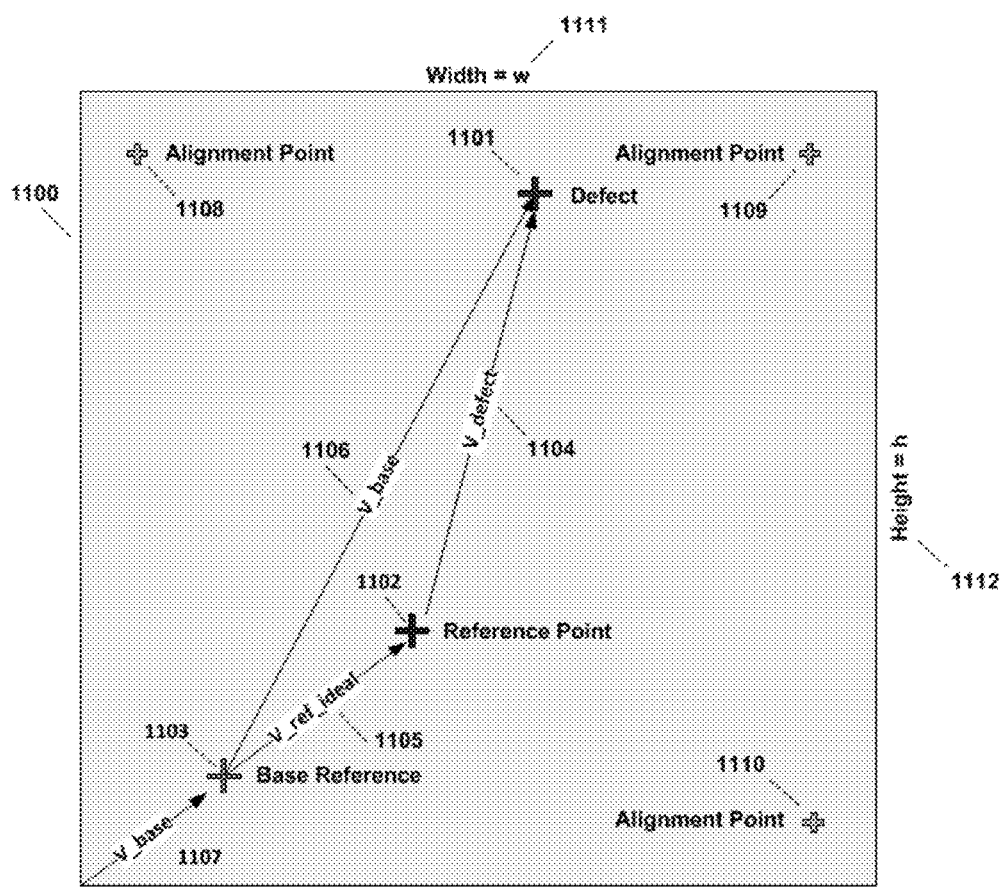
FIG. 11. shows a relationship between the defect coordinate system and common base reference coordinate system.

FIG. 11., shows a relationship between the defect coordinate system and common base reference coordinate system. All defect coordinates 1101 in an inspection record are generally given with respect to some arbitrary reference point 1102. The X & Y coordinates of this reference point 1102 are reported with respect to an origin located at the bottom left corner of the mask. However the location of the reference point with respect to the lower left corner of the mask, depends how accurately the mask was placed onto the stage. For example to achieve an accurate coordinate transformation, the origin of the mask and the stage would have to coincide with no gaps in-between. However, in reality, a small particle or a tiny gap between the bottom or left sides of the mask may occur and cause an offset. This can severely alter the reported distance between the inspection reference point 1102 and the bottom corner of the mask.

To eliminate this inaccuracy, an idealized location of the reference point 1102, instead of the location reported by the inspection tool is used. The idealized location of the reference point 1102 is obtained from the original design database. This technique ensures that the origin of the idealized pattern database, one which is free of any error, is always used, and not that the inspection stage. This eliminates the need to use the origin of the bottom corner of the physical mask thereby eliminating any error induced by any gaps caused between the mask and the stage.

It is not guaranteed that the mask be placed directly parallel to the axes of the stage of the inspection system. In such cases, stage coordinates of two or more alignment points 1106, 1107 & 1108 may be used to derive a micro rotation matrix $R_{micro}$ to correct for this slight tilt.

Furthermore it is very common for inspection systems to inspect masks in a rotated orientation, where the rotation may be −90, 180 or +90 degrees. In such cases the coordinates of the defects need to be rotated to a common upright orientation using a function $F_{upright}$, which is a function of the inspected mask orientation $\phi$, the design (ideal) distance from the bottom left corner of the mask and the base reference point 1103, the optical reduction factory R, as well as the mask width 1109 and height 1110. Thus the full transformation to rotate and translate the defect coordinates to a common base reference frame may be written as $$V_{base} = F_{upright}[R_{micro} \cdot V_{defect} + V_{ref\_ideal}]$$

where $V_{defect}$ is the original defect coordinate 1104 reported by the inspection system, $V_{base}$ is the defect represented in the base coordinate system in a common upright orientation, $V_{ref\_ideal}$ is the ideal distance from the base reference point to the inspection reference point that the inspection system reported the defect coordinates with respect to. $R_{micro}$ is an orthonormal rotation matrix or a quaternion transformation that is a function of two of more alignment points defined as $$R_{micro} = f(AlignPt\_1, AlignPt\_2, \ldots, AlignPt\_N)$$

Finally the function $F_{upright}$ is defined as a function of $$F_{upright} = f(\phi, V_{base}, w, h, R)$$

In a given embodiment the parser may simply ensure that all required fields to transform the defect coordinates into a base reference frame are collected and placed into the database or the parser may transform the defect coordinates into the base reference frame before saving them into the relational database.

FIG. 12. shows results from defect 332 through 353 from a given inspection records tracked against other inspections of the same mask. A defect may be reported using different numbers in various repeated inspection of the same mask. For example, defect 353 from the inspection number 8773526, has been matched against defect numbers 352, 352, 357 and 352 from the inspection reports 8773481, 8773405, 8773322 and 8773276 respectively. Although the defects number used to represent the same defect are not always identical, the matching is based on the coordinates of the defects expressed the common reference frame.

Figure 13:
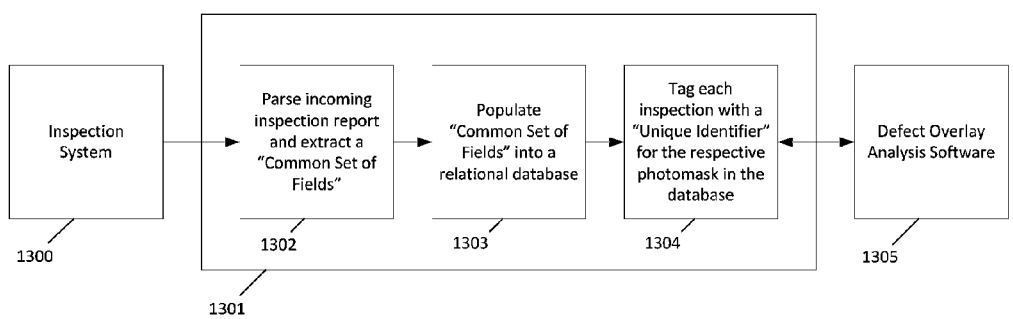
FIG. 13 shows the process of an inspection report being archived into a relational defect database.

FIG. 13 shows the process by which the database is populated using data from various inspection systems. An inspection system 1300 writes a defect report in its own file format to the relational defect database 1301.

Software of the database server 1302 parses the inspection report to yield a common set of fields required for the analysis. For example this includes the defect coordinates, the location of the reference and alignment points, the orientation in which the mask was inspected, and various other fields required to identify the mask.

At step 1303, the common sets of fields are populated into the relational database. Thus the database only comprises of the common set of fields, that are no longer dependent on the distinct file formats used by the inspection systems to generate the reports.

Step 1304 consists of tagging each inspection report with a unique identifier for the mask. In one instance the unique identifier may already be present in the inspection report parsed. Other times various fields in the inspection report may be used to query the factory mask tracking system, to retrieve the unique identifier for tagging purposes. This database is now ready to be accessed by the defect overlay analysis software 1305, installed at the users workstation.

Figure 14:
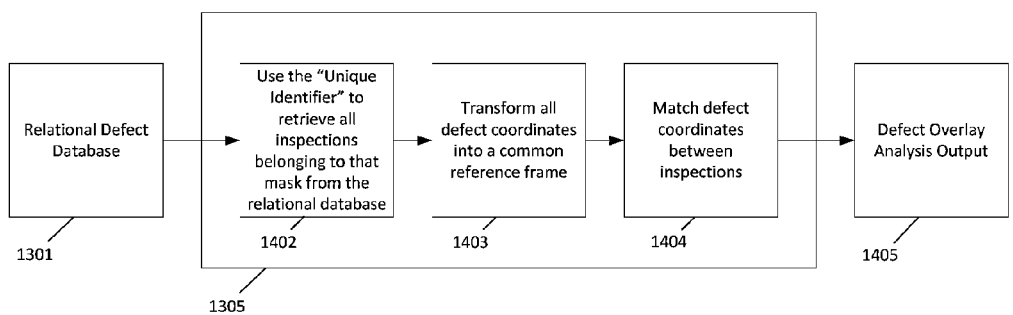
FIG. 14 shows the process of retrieving inspection report for the same mask from a relational defect database and performing the defect analysis.

FIG. 14 shows the process used by the defect overlay software 1305 to match defects between the various repeated inspections of the same mask. The defect overlay software 1401, commonly referred to as the 'Client', queries the relational defect database 1301 using a unique identifier in step 1402. This query results in the retrieval of all inspection reports of the same mask.

In step 1403, all defect coordinates from each and every inspection report are transformed into a common reference frame. Finally in step 1404, all resulting defects coordinates within some matching tolerance are matched and reported at 1405.

Figure 15:
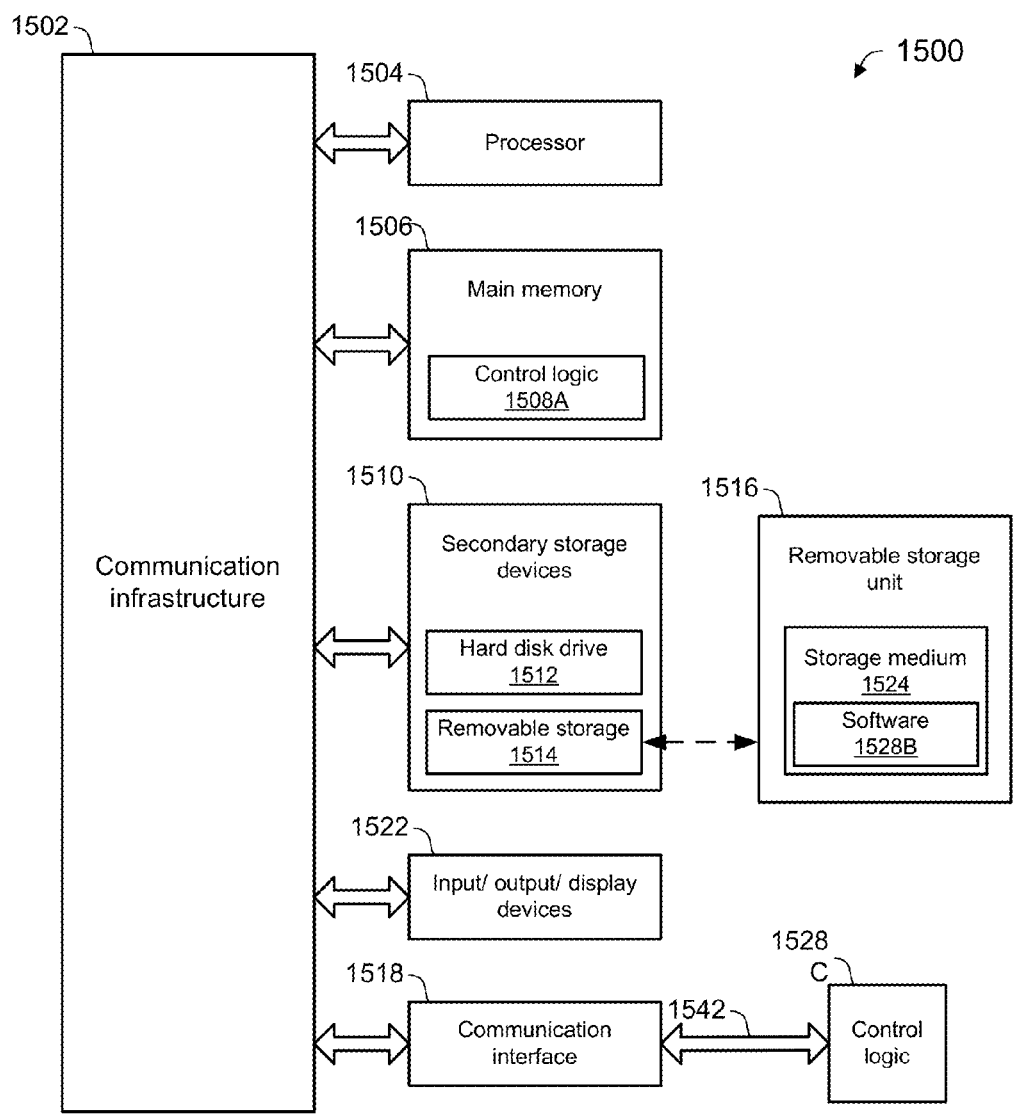
FIG. 15. shows computers/servers where the embodiments described herein may be implemented.

The embodiments described herein, including systems, methods/processes, and/or apparatuses, may be implemented using well known servers/computers, such as computer 1500 shown in FIG. 15. For instance, elements of example distributed storage system 801, including any of communication devices, and smart devices, depicted in FIG. 8 and elements thereof, each of the steps of flowcharts shown in FIGS. 13 and 14 can each be implemented using one or more computers 1500.

Computer 1500 can be any commercially available and well known computer capable of performing the functions described herein, such as computers available from International Business Machines, Apple, Sun, HP, Dell, Cray, etc. Computer 1500 may be any type of computer, including a desktop computer, a server, tablet PC, or mobile communication device, etc.

As shown in FIG. 15, computer 1500 includes one or more processors (e.g., central processing units (CPUs)), such as processor 1504. Processor 1504 is connected to a communication infrastructure 1502, such as a communication bus. In some embodiments, processor 1504 can simultaneously operate multiple computing threads.

Computer 1500 also includes a primary or main memory 1506, such as a random access memory (RAM). Main memory has stored therein control logic 1508AA (computer software), and data.

Computer 1500 also includes one or more secondary storage devices 1510. Secondary storage devices 1510 include, for example, a hard disk drive 1512 and/or a removable storage device or drive 1514, as well as other types of storage devices, such as memory cards and memory sticks. For instance, computer 1500 may include an industry standard interface, such as a universal serial bus (USB) interface for interfacing with devices such as a memory stick. Removable storage drive 1514 represents a floppy disk drive, a magnetic tape drive, a compact disk drive, an optical storage device, tape backup, etc.

Removable storage drive 1514 interacts with a removable storage unit 1516. Removable storage unit 1516 includes a computer useable or readable storage medium 15248 having stored therein computer software 1528B (control logic) and/or data. Removable storage unit 1516 represents a floppy disk, magnetic tape, compact disc (CD), digital versatile disc (DVD), Blue-ray disc, optical storage disk, memory stick, memory card, or any other computer data storage device. Removable storage drive 1514 reads from and/or writes to removable storage unit 1516 in a well known manner.

Computer 1500 also includes input/output/display devices 1522, such as monitors, keyboards, pointing devices, etc. Computer 1500 further includes a communication or network interface 1518. Communication interface 1518 enables computer 1500 to communicate with mobile devices. For example, communication interface 1518 allows computer 1500 to communicate over communication networks or mediums (representing a form of a computer useable or readable medium), such as local area networks (LANs), wide area networks (WANs), the Internet, etc. Network interface may interface with remote sites or networks by using wired or wireless connections. Examples of communication interface 1542 include but are not limited to a modem, a network interface card (e.g., an Ethernet card), a communication port, a Personal Computer Memory Card International Association (PCMCIA) card, etc.

Control logic 1528C may be transmitted to and from computer 1500 by using the communication medium. Any apparatus or manufacture comprising a computer useable or readable medium having control logic (software) stored therein is referred to herein as a computer program product or program storage device. This includes, but is not limited to, computer 1500, main memory 1506, secondary storage devices 1510, and removable storage unit 1516. Such computer program products, having control logic stored therein that, when executed by one or more data processing devices, because such data processing devices to operate as described herein, represent embodiments of the invention.

Although the present application has been described in connection with several embodiments, the application is not intended to be limited to the specific forms set forth herein. On the contrary, it is intended to cover such alternatives, modifications, and equivalents as can be reasonably included within the scope of the invention as defined by the appended claims.

What is claimed is:

1. A computer implemented method for tracking a repeated defect in a lithographic photomask that has undergone at least one photomask inspection using a plurality of inspection systems, wherein each photomask inspection has resulted in generating of an inspection report that includes information about defects in the photomask, the computer implemented method comprising:

translating a plurality of inspection reports that contain X and Y coordinates of a plurality of defects, wherein each inspection report reports the X and Y coordinates of a defect with respect to a non-standard origin that is specific to the mask inspection system used for generating that particular inspection report, by converting the X and Y coordinates of the non-standard origin into a new set of X and Y coordinates for a common origin, wherein the common origin is the same for the plurality of other inspection reports, wherein translating further includes converting other non-standard fields, such as orientation, into a common set of fields, such as common orientation, that are then populated into a relational database, wherein the common set of fields includes at a minimum horizontal and vertical die count, and horizontal and vertical inter die distance;

tagging each inspection report with a unique product code or field that can relate all inspection reports belonging to the same photomask or wafer;

matching all defects having coordinates that fall within a tolerance distance of defects flagged in prior inspection records of the same photomask or wafer, that have also undergone a similar translational and tagging step from the relational database, wherein, such matching comprises:

identifying defect A from inspection report A performed by inspection system A, identifying a defect B from a subsequent inspection report B performed by inspection system B, wherein defect A and defect B are the same defect that have been reported in inspection report A and inspection report B, wherein inspection system A and inspection system B are two separate types of inspection systems, wherein each inspection system having a defect reporting methodology that is distinct from the other inspection system, wherein such distinction includes each inspection system using a distinct reference point as it coordinate frame origin, and reporting the defect as a repeated defect if defect A and defect B are within a tolerance distance of each other, and enabling overlaying of inspection reports such that any repeating defects can be distinguished from non-repeating defects, and applying additional repair as needed.

2. The computer implemented method of claim 1, further comprising accessing inspection reports of the same mask from a plurality of defect databases.

3. The computer implemented method of claim 1, wherein the inspection report contains defect information from a die-to-die inspection, the method further comprising:

translating the defect X and Y coordinates to every die in the scanning direction by an amount equal to the die-pitch, transforming the X and Y defect coordinates to the base reference frame, and tracking against defects from other inspection reports of the same photomask.

4. The computer implemented method of claim 1, wherein one inspection report utilizes a mask orientation for reporting a defect that is different from the mask orientation utilized by another inspection report.

5. The computer implemented method of claim 1, wherein one inspection report utilizes a reference frame for reporting a defect that is different from the reference frame utilized by another inspection report.

6. The computer implemented method of claim 1, wherein one inspection report is generated utilizing an inspection system that is different in brand or model from the inspection system utilized to generate the other inspection report.

7. A physical and tangible computer-readable medium for storing computer readable instruction, the computer readable instructions performing a method for tracking a repeated defect from a variety of mask and wafer inspection systems, the computer readable medium comprising:

instructions for translating a plurality of inspection reports that contain X and Y coordinates of a plurality of defects, wherein each inspection report reports the X and Y coordinates of a defect with respect to a non-standard origin that is specific to the mask inspection system used for generating that particular inspection report, by converting the X and Y coordinates of the non-standard origin into a new set of X and Y coordinates for a common origin, wherein the common origin is the same for the plurality of other inspection reports, wherein translating further includes converting other non-standard fields, such as orientation, into a common set of fields, such as common orientation, that are then populated into a relational database, wherein the common set of fields includes at a minimum horizontal and vertical die count, and horizontal and vertical inter die distance;

instructions for tagging each inspection report with a unique product code or field that can relate all inspection reports belonging to the same photomask or wafer;

instructions for matching all defects having coordinates that fall within a tolerance distance of defects flagged in prior inspection records of the same photomask or wafer, that have also undergone a similar translational and tagging step from the relational database; and instructions for enabling overlaying of inspection reports such that any repeating defects can be distinguished from non-repeating defects;

and applying additional repair to as needed.

8. The physical and tangible computer-readable medium of claim 7, wherein the computer readable instructions are located on a mobile device.

9. The physical and tangible computer-readable medium of claim 7, wherein the computer readable instructions can be accessed through the worldwide internet.

* * * * *